United States Patent
Laube

(10) Patent No.: US 9,835,567 B2
(45) Date of Patent: Dec. 5, 2017

(54) METHOD FOR MONITORING THE OPERATIONAL STATE OF A SURFACE INSPECTION SYSTEM FOR DETECTING DEFECTS ON THE SURFACE OF SEMICONDUCTOR WAFERS

(71) Applicant: SILTRONIC AG, Munich (DE)

(72) Inventor: Frank Laube, Burghausen (DE)

(73) Assignee: SILTRONIC AG, Munich (DE)

( * ) Notice: Subject to any disclaimer, the term of this patent is extended or adjusted under 35 U.S.C. 154(b) by 189 days.

(21) Appl. No.: 14/803,173

(22) Filed: Jul. 20, 2015

(65) Prior Publication Data
US 2016/0041107 A1 Feb. 11, 2016

(30) Foreign Application Priority Data
Aug. 8, 2014 (DE) .......... 10 2014 215 727

(51) Int. Cl.
| | |
|---|---|
| *G01N 21/00* | (2006.01) |
| *G01N 21/88* | (2006.01) |
| *G01N 21/95* | (2006.01) |
| *G01N 21/93* | (2006.01) |

(52) U.S. Cl.
CPC ......... *G01N 21/8851* (2013.01); *G01N 21/93* (2013.01); *G01N 21/9501* (2013.01); *G01N 2021/8854* (2013.01)

(58) Field of Classification Search
CPC . G01N 21/8851; G01N 21/9501; G01N 21/93
See application file for complete search history.

(56) References Cited

U.S. PATENT DOCUMENTS

| | | | |
|---|---|---|---|
| 4,644,172 A | 2/1987 | Sandland et al. | |
| 6,515,742 B1* | 2/2003 | Ruprecht ........... | G01N 21/9501 356/237.4 |
| 7,027,146 B1 | 4/2006 | Smith et al. | |
| 7,084,965 B2 | 8/2006 | Wienecke et al. | |
| 2007/0003478 A1 | 1/2007 | Becker et al. | |
| 2007/0030478 A1* | 2/2007 | Kim ................... | G01N 21/9501 356/237.2 |
| 2010/0208979 A1 | 8/2010 | Abbott et al. | |

\* cited by examiner

*Primary Examiner* — Michael P Stafira
(74) *Attorney, Agent, or Firm* — Brooks Kushman P.C.

(57) ABSTRACT

The operational state of a surface inspection system for detecting defects on the surface of semiconductor wafers is monitored by:
- providing a reference wafer having defects of a particular number, size, and density on an examination surface;
- conducting a reference inspection of the reference wafer and at least one control inspection of the reference wafer by the surface inspection system, the position and size of defects on the examination surface being measured;
- identifying defects which, because of their position, are regarded as common defects of the reference inspection and of the control inspection;
- for each common defect, determining a size difference obtained from comparing its size from the reference inspection and from the control inspection; and
- assessing the operational state of the surface inspection system on the basis of the size differences.

15 Claims, 3 Drawing Sheets

METHOD FOR MONITORING THE OPERATIONAL STATE OF A SURFACE INSPECTION SYSTEM FOR DETECTING DEFECTS ON THE SURFACE OF SEMICONDUCTOR WAFERS

CROSS-REFERENCE TO RELATED APPLICATIONS

This application claims priority to German Patent Application No. DE 102014215727.7 filed Aug. 8, 2014 which is herein incorporated by reference.

BACKGROUND OF THE INVENTION

1. Field of the Invention

The invention relates to a method for monitoring the operational state of a surface inspection system for detecting defects on the surface of semiconductor wafers.

2. Description of the Related Art

In the course of the preparation of semiconductor wafers to form substrates for the production of electronic components, surfaces of semiconductor wafers are examined for the presence of defects. The surface to be examined is usually the upper side surface of the semiconductor wafer, on which the formation of structures of electronic components is intended. In order to carry out the examination, scanning surface inspection systems may be used. These gradually illuminate the surface of the semiconductor wafer with a light spot of laser light and detect scattered light as a function of one or different solid angles (channels). The scattered light data obtained in this way allow information to be deduced about the position and size of defects which are present on the surface examined.

So that the information about the size of defects coincides as accurately as possible with the actual size of the defects, the surface inspection system is calibrated with the aid of a reference semiconductor wafer. U.S. Pat. No. 7,027,146 B1 describes a way in which reference semiconductor wafers can be produced. Reference semiconductor wafers are also available for purchase. A reference semiconductor wafer as described in U.S. Pat. No. 7,027,146 B1 has reference defects of different size, the number and size distribution of which is known, deposited on its surface. Polystyrene latex spheres (PSL spheres) are often used as reference defects. In the case of PSL spheres, the real diameter of the sphere observed corresponds to the reported size of the defect. If the reference defect does not have a spherical configuration, the size of the defect usually means its largest spatial extent.

If the surface inspection system is properly calibrated, it indicates the number, position and the size of the defects on the reference semiconductor wafer with an accuracy that varies in terms of size within a specified tolerance limit (calibration tolerance). The measurement data obtained may, for example, be processed as a histogram which represents the frequency of the defects as a function of their size. The processing of measurement data may be restricted to size intervals, so that measurement data which relate to defects with a size lying outside a size interval are not taken into account.

It is important to monitor whether a surface inspection system is in a proper operational state, and if appropriate to warn if the monitoring reveals anomalies. If anomalies occur, their cause must be investigated, and if appropriate the proper state of the surface inspection system must be restored. U.S. 2007/0030478 A1 describes a monitoring method which provides repeated examination of a reference semiconductor wafer in the course of the use of the surface inspection system. If the measurement data of an examination of the reference semiconductor wafer do not differ substantially from those which the surface inspection system delivers in the freshly calibrated state, the state of the surface inspection system is regarded as in order. However, the scope and sensitivity of the examinations described leaves something to be desired. For instance, by measuring the number of defects no information is obtained about the stability of the measurement of defect sizes as a function of time. A possible drift of the defect size assigned to a defect by the surface inspection system is not noticed, or is only noticed late. In this regard, the information content remains insufficient, even if additional information is gathered about the position of the maximum of the size distribution and its variation as a function of time.

SUMMARY OF THE INVENTION

It is therefore the object of the present invention to provide a corresponding method which allows monitoring of the operational behavior of a surface inspection system for detecting defects on surfaces of semiconductor wafers more comprehensively and with better sensitivity. These and other objects are achieved by a method for monitoring the operational state of a surface inspection system for detecting defects on the surface of semiconductor wafers, comprising:

provinding a reference semiconductor wafer having defects of a particular number and size and density on an examination surface of the reference semiconductor wafer;

conducting a reference inspection of the reference semiconductor wafer and at least one control inspection of the reference semiconductor wafer by using the surface inspection system, the position and size of the defects on the examination surface being measured;

identifying defects which, because of their position, are regarded as common defects of the reference inspection and of the control inspection; for each common defect, determining of a size difference which is obtained from a comparison of its size on the basis of the reference inspection and the control inspection; and assessing the operational state of the surface inspection system on the basis of the size differences determined.

BRIEF DESCRIPTION OF THE DRAWINGS

Some aspects of the invention will be explained in more detail below with reference to the drawings.

DETAILED DESCRIPTION OF THE PREFERRED EMBODIMENT(S)

Figure 1:
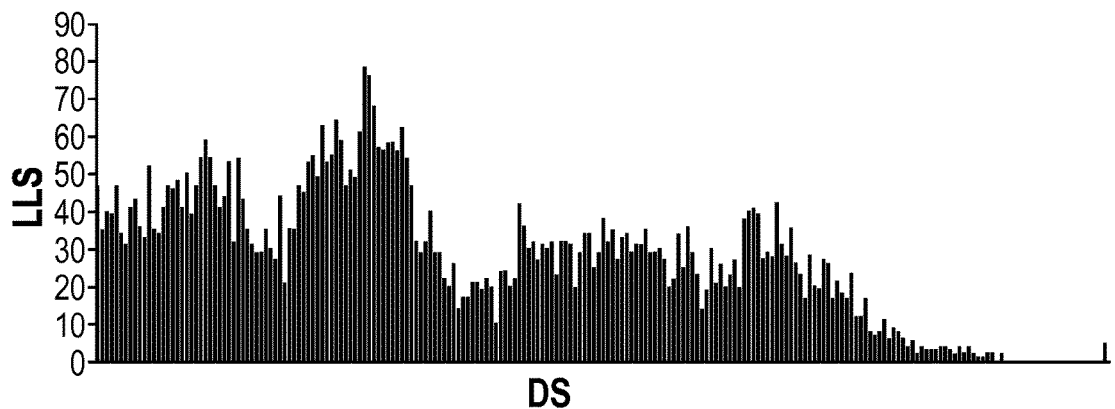
FIG. 1 shows the size distribution of defects on a reference semiconductor wafer.

The method according to the invention is not restricted to observing one or more of the following parameters and their development in the course of operation of the surface inspection system: the number of defects detected, the position of the maximum of the size distribution of detected defects, and the width of the size distribution of detected defects in a specified size interval. Rather, it involves detection of the size of individual defects and determination of size differences of those defects which result from a comparison of the defect sizes according to the reference inspection and the control inspection. The operational state of the surface inspection system is assessed on the basis of these size differences which have been determined.

The surface inspection system comprises a light source which generates a light beam, with which an examination surface is scanned, and one or more detectors which register scattered light resulting from the interaction between defects and the light beam. Such surface inspection systems are commercially available, for example from the manufacturer KLA-Tencor.

The reference inspection is preferably carried out in the course of calibration or immediately after calibration of the surface inspection system. Before a subsequent calibration, one or more control inspections take place in order to obtain a picture of the operational state of the surface inspection system and implement measures if need be, in order to restore the surface inspection system to a proper state. Between the reference inspection and a first control inspection, and optionally between subsequent control inspections, the surface inspection instrument is used for its intended purpose, namely to detect defects on surfaces of semiconductor wafers.

In order to calibrate the surface inspection system, it is possible to use reference semiconductor wafers which have an examination surface, on which there are PSL spheres in a defined number and with a defined size distribution.

In principle, such a reference semiconductor wafer with PSL spheres may also be used as a reference semiconductor wafer for the reference inspection and the control inspection, which are carried out in the course of the method according to the invention. The defects of the reference semiconductor wafer preferably have a continuous size distribution, which is difficult to achieve with PSL spheres. It is therefore preferred to use a reference semiconductor wafer with defects that originate from vacancy agglomerations which have been formed during the crystallization of a single crystal, from which the reference semiconductor wafer is obtained. The single crystal preferably consists of silicon. The formation of vacancy agglomerations, which may for example be detected as COP defects, may be influenced during the crystallization of the single crystal at an interface with a melt. A high crystallization rate and a low temperature gradient at the interface between the melt and the growing single crystal promote the formation of such defects. The examination surface of the reference semiconductor wafer obtained from the single crystal is preferably in the polished state. The examination surface of the reference semiconductor wafer is that surface which is scanned in the course of the reference inspection and the control inspection. In contrast to reference semiconductor wafers with PSL spheres, the preferred reference semiconductor wafer is less sensitive and can be cleaned without problems. The density of the defects on the examination surface of the reference semiconductor wafer is preferably not less than $1/cm^2$ and not more than $15/cm^2$.

In the course of the reference inspection and the control inspection, at least the position and size of defects on the examination surface of the reference semiconductor wafer are measured. Common defects of the reference inspection and of the control inspection are subsequently identified. These are those which can be regarded as identical on the basis of their position. A suitable procedure for finding common defects is described in the standard SEMI M50-0307. Accordingly, common defects of the reference inspection and of the control inspection are such defects as are separated from one another in terms of their position by no more than a predefined distance (search radius) with no further defect being found within this distance.

According to the invention, the size of a common defect according to the reference inspection is compared with the size of this defect according to the control inspection. The size difference determined by the comparison is registered for each of the common defects identified, and this information is used as a basis for assessing the operational state of the surface inspection system.

This information is a reliable indicator which makes it possible to promptly recognize changes in the operational state of the surface inspection system, such as a drift of the defect size assigned to a defect by the surface inspection system. It is therefore preferably used for the purpose of statistical process control (SPC).

Such use may be carried out in a variety of ways, for example by calculating the average size difference for one or more size intervals of for the entire size spectrum of the common defects and registering its development in the course of successive control inspections. A tolerance corridor, within which a registered average size difference is regarded as noncritical, is furthermore defined by a lower and an upper threshold. If the registered average size difference departs from the tolerance corridor, this process is taken as a reason to assess the operational state of the surface inspection system as anomalous. When this event occurs, it is expedient to investigate the reasons of the development found for the average size difference without delay, and if need be restore a proper state of the surface inspection system. Optionally, a warning signal which signals the occurrence of this event may be generated. The distance between the lower and upper thresholds of the tolerance corridor is preferably not greater than the calibration tolerance of the respective size interval.

Another possibility for evaluation of the information obtained about the size difference of common defects is, for example, to plot the size differences determined against the defect sizes which were measured in the course of the reference inspection, and to define tolerance limits within which the status of the surface inspection system may be regarded as not anomalous.

In addition, the number of common defects identified may be registered and the development of this parameter as a function of time may be observed in the course of successive control inspections. Anomalies in the development of this parameter may be taken as a reason to check whether the surface inspection system is still in a proper state.

As an additional measure, in the course of the reference inspection and the control inspection, or the control inspections, the total number of defects may be identified and the development of the total number as a function of time may be observed, optionally within one or more size intervals, in order to be able to ascertain whether the above-mentioned calculation of the average size difference is being done on a statistically meaningful basis.

The method according to the invention is also distinguished by a certain robustness in terms of possible contamination of the reference semiconductor wafer in the course of the method. By virtue of this robustness, it is not always necessary to have to clean the contaminated reference semiconductor wafer first, before a control inspection can take place. Often, the result of the contamination is merely that a smaller number of common defects is identified. This result is unimportant, so long as the number of common defects identified remains significant for a statistical evaluation. On the other hand, a reduction in the number deemed critical may be taken as a reason to clean the reference semiconductor wafer before planned reuse.

FIG. 1 shows a typical histogram of the size distribution of light-scattering defects (LLS) which were found on a reference semiconductor wafer by examination with a surface inspection system in a detection channel of the surface inspection system. The frequency of the defects is plotted against their size (DS). The reference semiconductor wafer examined is a polished semiconductor wafer of silicon. The light-scattering defects are defects which are attributable to the presence of vacancy agglomerations.

Figure 2:
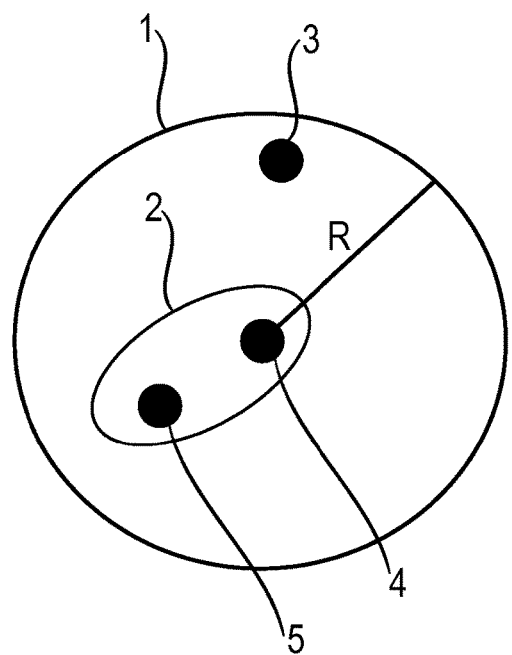
FIG. 2 schematically shows an observation window within which a common defect has been identified.

FIG. 2 shows a circular observation window 1 with a radius R (search radius), within which defects 3, 4 and 5 were found. In the example represented, defect 5 has the size $s_0$ and the position coordinates $(x_0,y_0)$. The index 0 is intended to indicate that the defect was found in the course of a reference inspection. Defect 4 has the size $s_n$ and the position coordinates $(x_n,y_n)$. The index n is intended to indicate that the defect was found in the course of an $n^{th}$ control inspection. Defect 3 is a further defect within the radius R with a particular position and size, which was found in the course of the reference inspection or the $n^{th}$ control inspection. If a further defect such as defect 3 is found, defects 3, 4 and 5 are not taken into account because they cannot be assigned uniquely. If only defects 4 and 5 are found within the radius R, they are considered as a common defect 2 because of their position. According to the invention, the size difference is determined between the size of the common defect which is found from the reference inspection and the size of the common defect which is found according to the control inspection. With reference to FIG. 2, the size difference of defects 5 and 4 is thus to be determined, if there is not a further defect such as defect 3.

Figure 3:
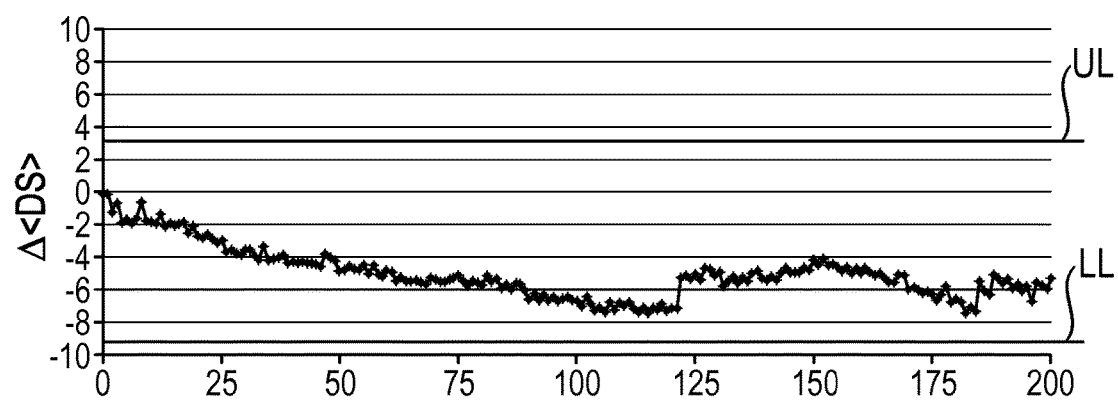
FIG. 3 shows a control map for monitoring of the operational state of a surface inspection system.
Figure 4:
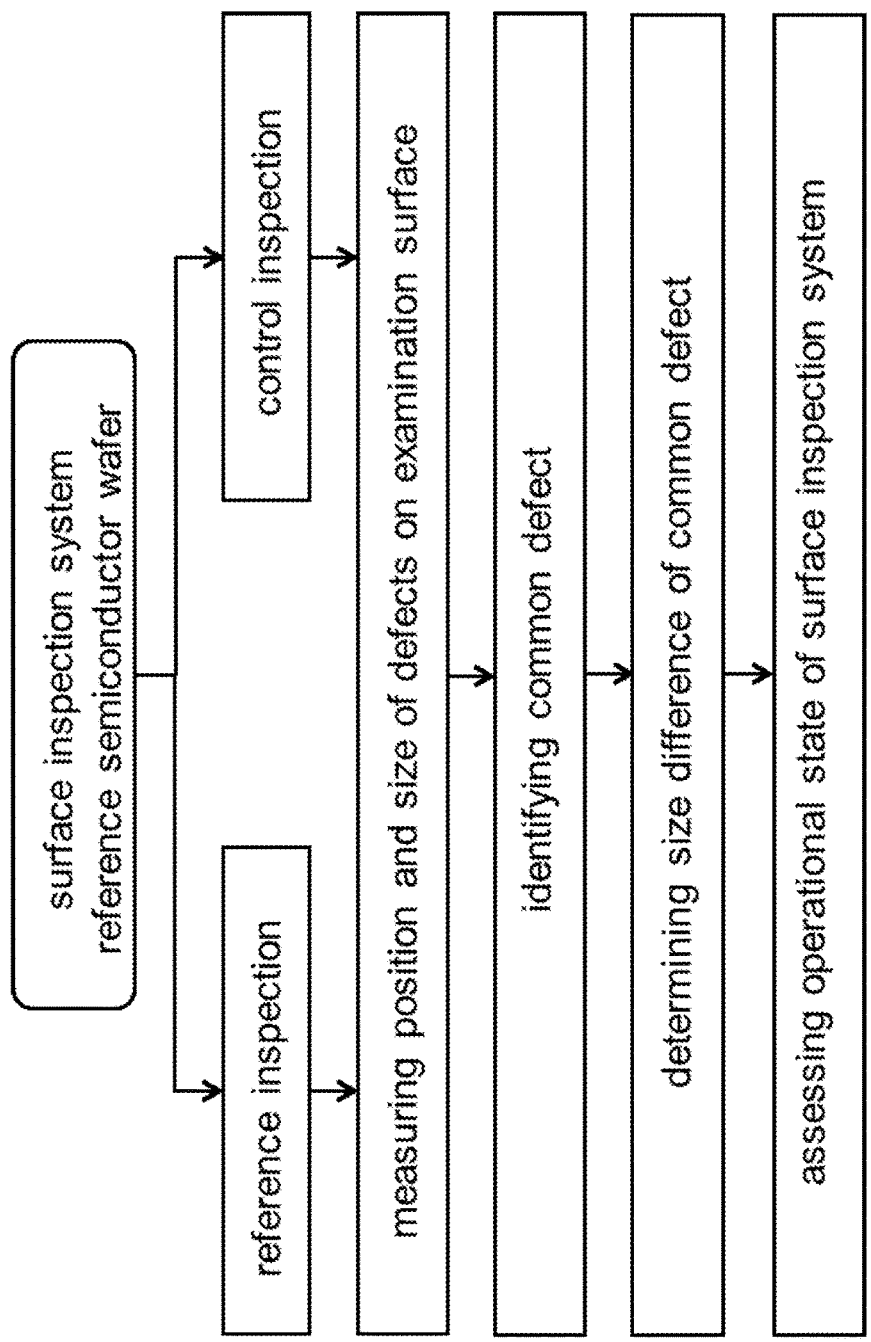
FIG. 4 illustrates a flow chart for one embodiment of the method of the invention.

FIG. 3 shows a typical control map such as may be used for monitoring the operational state of a surface inspection system. In this control map, the average size difference $\Delta\langle DS\rangle$ of common defects is plotted against the running number # of control inspections for a particular size interval. The lower threshold LL and the upper threshold UL of a tolerance corridor are also indicated.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for monitoring the operational state of a surface inspection system for detecting defects on the surface of semiconductor wafers to determine whether the operational state is a proper state for detecting defects on semiconductor wafers, comprising:
    providing a surface inspection system including at least one light source directed at the surface of a wafer and at least one detector which detects scattered light from the wafer surface,
    providing a reference semiconductor wafer having defects of a particular number and size and density on an examination surface of the reference semiconductor wafer;
    conducting a reference inspection of the reference semiconductor wafer and at least one control inspection of the reference semiconductor wafer by scanning the wafer surface using the surface inspection system, and measuring and recording the position and size of the defects on the examination surface;
    identifying one or more defects which, because of their position, are regarded as common defects of the reference inspection and of the control inspection;
    for each common defect, determining a size difference which is obtained from comparing the size of the common defect on the basis of the reference inspection and the control inspection; and
    assessing the operational state of the surface inspection system on the basis of the size difference or differences determined, wherein the assessment of the operational state of the surface inspection system is anomalous if the average of the size differences lies in a size interval outside a tolerance corridor, wherein if the operational state is determined to be faulty, restoring the surface inspection system to a proper operational state.

2. The method of claim 1, wherein the difference between a lower and an upper threshold of the tolerance corridor is not greater than a calibration tolerance in the size interval.

3. The method of claim 1, comprising generating a warning signal if the operational state of the surface inspection system is assessed as anomalous.

4. The method of claim 1, wherein the defects on the examination surface of the reference semiconductor wafer have a continuous size distribution.

5. The method of claim 2, wherein the defects on the examination surface of the reference semiconductor wafer have a continuous size distribution.

6. The method of claim 1, wherein the defects on the examination surface of the reference semiconductor wafer have a density which is not less than $1/cm^2$ and not greater than $15/cm^2$.

7. The method of claim 2, wherein the defects on the examination surface of the reference semiconductor wafer have a density which is not less than $1/cm^2$ and not greater than $15/cm^2$.

8. The method of claim 4, wherein the defects on the examination surface of the reference semiconductor wafer have a density which is not less than $1/cm^2$ and not greater than $15/cm^2$.

9. The method of claim 1, wherein the reference semiconductor wafer is obtained from a single crystal and the defects on the examination surface originate from vacancy agglomerations which have been formed during crystallization of the single crystal.

10. The method of claim 2, wherein the reference semiconductor wafer is obtained from a single crystal and the defects on the examination surface originate from vacancy agglomerations which have been formed during crystallization of the single crystal.

11. The method of claim 3, wherein the reference semiconductor wafer is obtained from a single crystal and the defects on the examination surface originate from vacancy agglomerations which have been formed during crystallization of the single crystal.

12. The method of claim 4, wherein the reference semiconductor wafer is obtained from a single crystal and the defects on the examination surface originate from vacancy agglomerations which have been formed during crystallization of the single crystal.

13. The method of claim 6, wherein the reference semiconductor wafer is obtained from a single crystal and the defects on the examination surface originate from vacancy agglomerations which have been formed during crystallization of the single crystal.

14. In a process for the surface examination of semiconductor wafers to detect surface defects on the wafers wherein a surface inspection system containing at least one source of laser light which scans the wafer surface and at least one detector which detects light scattered from the wafer surface is used, wherein an operational state of the surface inspection system is assessed by inspection of a reference wafer, the improvement comprising:

provide a reference semiconductor wafer having defects of a particular number and size and density on an examination surface of the reference semiconductor wafer:

conducting a reference inspection by scanning the reference semiconductor wafer and at least one control inspection by a further scanning of the reference semiconductor wafer by using the surface inspection system, and measuring and recording the position and size of the defects on the examination surface being measured;

identifying one or more defects which, because of their position on the reference semiconductor wafer, are regarded as common defects of the reference inspection and of the control inspection;

for each common defect, determining a size difference which is obtained by comparing the sizes of the common defect on the basis of the reference inspection and the control inspection; and assessing the operational state of the surface inspection system on the basis of the size difference or differences determined, and if the operational state is determined to be proper, scanning at least one semiconductor wafer for surface defects, and if the operational state is determined to be anomalous, restoring the operational state to a proper operational state, and scanning at least on semiconductor wafer for surface defects.

15. The method of claim 14, wherein the assessment of the operational state of the surface inspection system is anomalous if the average of the size differences lies in a size interval outside a tolerance corridor.

* * * * *